United States Patent [19]

Komatsu et al.

[11] Patent Number: 5,395,239
[45] Date of Patent: Mar. 7, 1995

[54] OCCLUSION PRESSURE DETECTING SHEET

[75] Inventors: Tomoaki Komatsu; Kiyohiko Nouno; Shotaro Nakanishi; Yoshiko Watanabe, all of Tokyo, Japan

[73] Assignee: Fuji Photo Film Co., Ltd., Kanagawa, Japan

[21] Appl. No.: 136,242

[22] Filed: Oct. 15, 1993

[51] Int. Cl.6 .............................................. A61C 19/04
[52] U.S. Cl. ........................................ 433/68; 433/71
[58] Field of Search ............................. 433/68, 70, 71; 128/777; 73/762, 379.02

[56] References Cited

U.S. PATENT DOCUMENTS

| | | | |
|---|---|---|---|
| 3,469,439 | 9/1969 | Roberts et al. | 73/762 |
| 3,813,781 | 6/1974 | Fargione | 433/68 |
| 3,959,881 | 6/1976 | Kokal, Jr. | 433/70 |
| 4,002,060 | 1/1977 | Ogata et al. | 73/141 R |
| 4,132,112 | 1/1979 | Hosoi et al. | 73/141 R |
| 4,142,404 | 3/1979 | Ogata et al. | 73/762 |
| 4,580,977 | 8/1986 | Ames | 433/68 |

Primary Examiner—Cary E. O'Connor
Attorney, Agent, or Firm—Sughrue, Mion, Zinn, Macpeak & Seas

[57] ABSTRACT

A pressure-sensitive recording sheet, comprising: a synthetic resin support sheet; a color developer layer coated on one face of the support sheet; a color former layer overcoated on the color developer layer and containing a microcapsulated color former; a first water-impermeable layer adhering on the other face of the support sheet through an adhesive; and a transparent second water-impermeable layer covering directly over the color former layer; and wherein the outer peripheries of the first and second water-impermeable layers are liquid-tightly closed to protect the support sheet, the color developer layer and the color former layer from attack by any aqueous liquid. The pressure-sensitive recording sheet or the support sheet is shaped to have a horseshoe-like contour to be used as an occlusion pressure detecting sheet. A wax coating layer may be provided on at least one surface of the occlusion pressure detecting sheet to record the dental arch pattern.

12 Claims, 6 Drawing Sheets

OCCLUSION PRESSURE DETECTING SHEET

BACKGROUND OF THE INVENTION

1. Field of the Invention

The present invention relates to a pressure-sensitive recording sheet which senses the pressure applied thereon by the change in color density, and an occlusion pressure detecting sheet used by a dentist for the measurement of the occlusion pressure and condition of a patient.

2. Prior Art

A pressure-sensitive recording sheet composed of a support sheet coated with a color developer and a color former overcoated on the color developer layer has been known in the art (reference should be made, for example, to Japanese Patent Publication Nos. 24852/1982 (corresponding to U.S. Pat. No. 4,132,112) and 16654/1984 (corresponding to U.S. Pat. No. 4,002,060)).

However, this known pressure-sensitive recording sheet has a disadvantage that the pressure applied thereon cannot be sensed precisely when the color former is wetted with water. To overcome such a disadvantage, it has been conceived to cover the sheet with a transparent waterproof sheet. For example, Japanese Utility Model Publication No. 8166/1970 discloses a structure wherein a waterproof layer is formed by laminating a polyethylene layer or by coating an emulsion of a vinylidene chloride copolymer on one face of a transparent paper sheet (serving as a support), and microcapsules of a color former are coated on the other face of the transparent paper sheet, the sheet being bent to form an envelope such that the face coated with the microcapsules of the color former spreads as the interior faces, between which a proper leaf of intermediate or underlying paper coated with a color developer is contained, followed by sealing the outer periphery of the envelope by the use of an adhesive.

Unexamined Japanese Patent Publication Nos. 68513/1977 and 24314/1976 disclose an alternative structure wherein protective layers are laminated over the pressure-detecting faces of the recording sheet so that the sheet structure has the waterproof property.

However, in the prior art structure wherein one face of a transparent paper sheet is protected by a waterproof layer while the other face being applied with the microcapsule layer and an envelope is formed by the such composite laminated structure followed by sealing of the outer periphery of the envelope, the microcapsule layer is interposed, together with the adhesive, between the folded two layers of the transparent paper sheet at the marginal portions of the envelope. As the result, adhesion of the entire envelope structure becomes unreliable. In addition, tight adhesion between the transparent paper sheet and the intermediate or underlying sheet cannot be expected, and there is also another problem of delamination when it is in use.

The other prior art technique of laminating, by heat seal, the protection layer over the recording sheet has a disadvantage that the property of the recording sheet is deteriorated by the application of heat, leading to reduction in color developing property.

On the other hand, in the field of dental treatment, carbon paper has been widely used to know the occlusion condition of the teeth of a patient. Carbon paper is inserted between the upper and lower dental arches of the patient; and as the patient bites strongly to occulude the upper and lower teeth, carbon particles adhere on the occlusal surface at the portions where the upper and lower teeth are abutted. The dentist can diagnose the occlusion condition of the teeth of the patient by observing the positions and areas of the portions to which carbon particles stick.

However, by this prior art of using carbon paper, it is merely possible to detect the portions where the upper and lower teeth abut with each other, and precise detection of occlusion pressure cannot be done by the use of carbon paper. Under such circumstance, the dentist should estimate the occlusion pressure by observing the sticking condition of carbon particles, leading to the problem that the precise diagnosis of occlusion condition of the teeth of the patient cannot be made, leading to difficulty in determination of subsequent dental treatment course.

Another problem of the prior art, in which carbon paper is used, is that it becomes necessary to impinge the upper and lower teeth for plural times or to rub the portions of carbon paper which contact teeth by the tooth tips, for example, by offseting the upper and lower jaws and then sliding them laterally.

The prior art technology has another problem that the dentist must precisely position the detecting sheet, such as carbon paper, by looking into the oral cavity of the patient since there is provided no means for precisely positioning the detecting sheet so as to know the portions, at which upper and lower teeth contact or abut with each other. This leads to the problem that the operation efficiency is lowered.

OBJECTS AND SUMMARY OF THE INVENTION

The present invention has been accomplished under the circumstances as aforementioned, and a first object thereof is to provide a pressure-sensitive recording sheet in which the recording sheet structure is completely sealed to have realible waterproof property without the fear of delamination or exfoliation between the recording sheet structure and the liquid-tight protection layer and without the fear of deterioration due to heating.

An additional or second object of this invention is to provide an occlusion pressure detecting sheet for detecting the tooth alignment condition in the dental arch and the distribution of the occlusion pressure of a patient simply and precisely to obtain data which can be used as extremely effective data for the precise diagnosis on the occlusion condition and for the determination of a treatment course, by a relatively comfortable operation for the patient on one hand and on the other hand through a simple operation by the dentist.

The first object of the invention is attained by the provision of a pressure-sensitive recording sheet, comprising:

(a) a synthetic resin support sheet;
(b) a color developer layer coated on one face of said support sheet;
(c) a color former layer overcoated on said color developer layer and containing a microcapsulated color former;
(d) a first water-impermeable layer adhering on the other face of said support sheet through an adhesive; and
(e) a transparent second water-impermeable layer covering directly over said color former layer; and wherein the outer peripheries of said first and second water-impermeable layers are liquid-tightly closed to protect said support sheet, said color developer layer and said color former layer from attack by any aqueous liquid.

In more detail, the backside, which is the side or face opposed to the side or face on which the color developer is coated, of the support sheet is allowed to adhere to the first water-impermeable layer (or the backside waterproof layer), the color former layer directly covered by the second water-impermeable layer (or the obverse waterproof layer), and the first and second water-impermeable layers are liquid-tightly sealed around the outer periphery of the support sheet, whereby the entire sheet structure is perfectly sealed to ensure reliable waterproof construction. Since the first water-permeable layer (or the backside waterproof layer) is fixedly adhering to the support sheet, displacement or offset of the second water-impermeable layer (or the obverse waterproof layer) is restricted to prevent delamination thereof from the recording sheet. Since both water-impermeable layers are sealed by the use of an adhesive to eliminate heating, otherwise necessary in the prior art laminating processing, deterioration in property of the recording sheet and/or deterioration in coloring is prevented.

In a preferred embodiment, the support sheet and the first and second water-impermeable layers are made of polyethylene terephthalate (PET), and the adhesive is coated on the first water-impermeable layer.

The second object of the invention is attained by the provision of an occlusion pressure detecting sheet, comprising:
(a) a synthetic resin support sheet having a horseshoe shape adapted to extend along the dental arch;
(b) a color developer layer co-extensively coated on one face of said support sheet;
(c) a color former layer overcoated on said color developer layer and containing a microcapsulated color former;
(d) a first water-impermeable layer adhering on the other face of said support sheet through an adhesive; and
(e) a transparent second water-impermeable layer covering directly over said color former layer; and
wherein the outer peripheries of said first and second water-impermeable layers are liquid-tightly closed to protect said support sheet, said color developer layer and said color former layer from attack by any aqueous liquid.

It is preferred that a positioning mark is provided for positioning the occlusion pressure detecting sheet in situ relative to the dental arch of the patient, or that lugs integrally protruding beyond the outer periphery of the occlusion pressure detecting sheet are provided to position the occlusion pressure detecting sheet in situ relative to the cuspids in the dental arch of the patient. It is also preferred that the occlusion pressure detecting sheet is provided with a tag integrally protruding from the substantial center of the sheet and/or a mark for identifying the patient.

In some case, the image of the occlusion pressure recorded on the occlusion pressure detecting sheet may be read by a scanner to obtain electric signals which are processed through a computer to effect image processing. During such processing, it often arises a case where the image cannot be read accurately due to the diffused reflection by the irregular surface condition. To cope with this problem, according to a preferred embodiment of the invention, a wax coating layer is provided on the exposed surface of the second water-impermeable layer (the obverse waterproof layer) to obviate the influences by the presence of irregular traces of teeth at the step of reading the image by the scanner, whereby the recording sheet is well accommodated for accurate read-out of the occlusion pressure.

The second object of the invention is attained alternatively by the provision of an occlusion pressure detecting sheet, comprising:
(a) a synthetic resin support sheet having a horseshoe shape adapted to extend along the dental arch;
(b) a color developer layer co-extensively coated on one face of said support sheet;
(c) a color former layer overcoated on said color developer layer and containing a microcapsulated color former;
(d) a first water-impermeable layer adhering on the other face of said support sheet through an adhesive;
(e) a transparent second water-impermeable layer covering directly over said color former layer; and
(f) a wax coating layer laminated over at least one of said first and second water-permeable layers;
whereby the occlusion pressure of the patient is detected by determining the density of color developed by the reaction between said color former and said color developer under the occlusion pressure of the patient, and the pattern of the dental arch of the patient is detected by observing the trace of the patient's teeth left on said wax coating layer.

It is desirous that the color developed in the pressure-sentive sheet is differentiated from the color of the wax coating layer, more preferably the wax coating layer has a color which is complementary, or almost complementary, the color developed by the reaction between said color former and said color developer.

BRIEF DESCRIPTION OF THE DRAWINGS

The above and other objects and advantages of the invention will become apparent from the following description of the presently preferred embodiments thereof with reference to the appended drawings in which.

EMBODIMENTS OF THE INVENTION

First Embodiment

Figure 1:
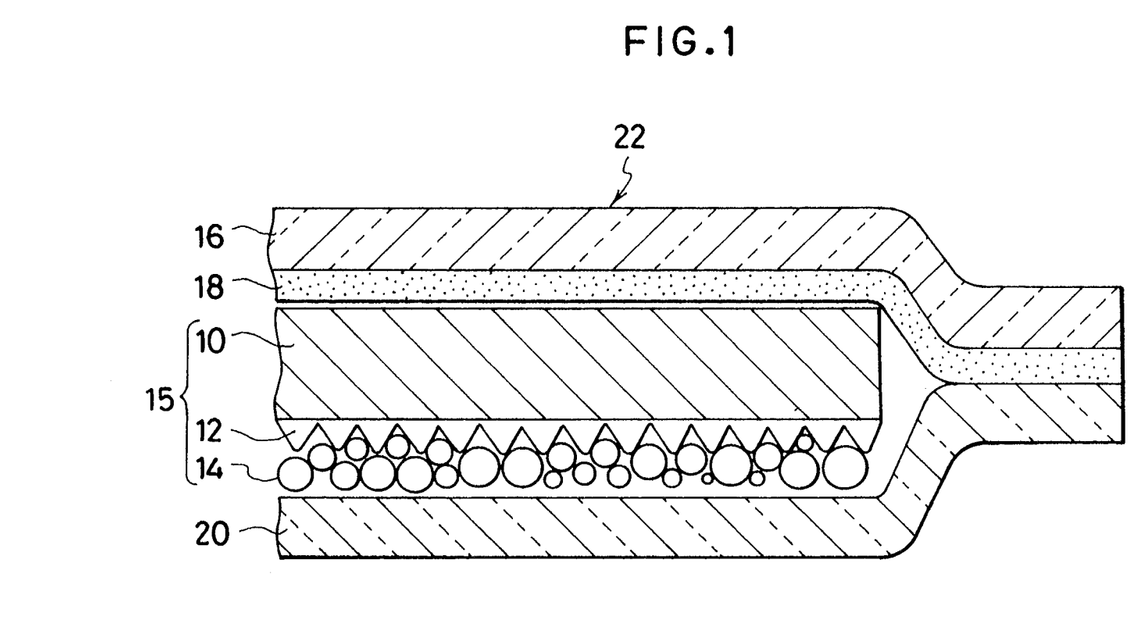
FIG. 1 is a sectional view showing a portion (marginal or peripheral portion) of the pressure-sensitive recording sheet according to the first embodiment of the invention.
Figure 2:
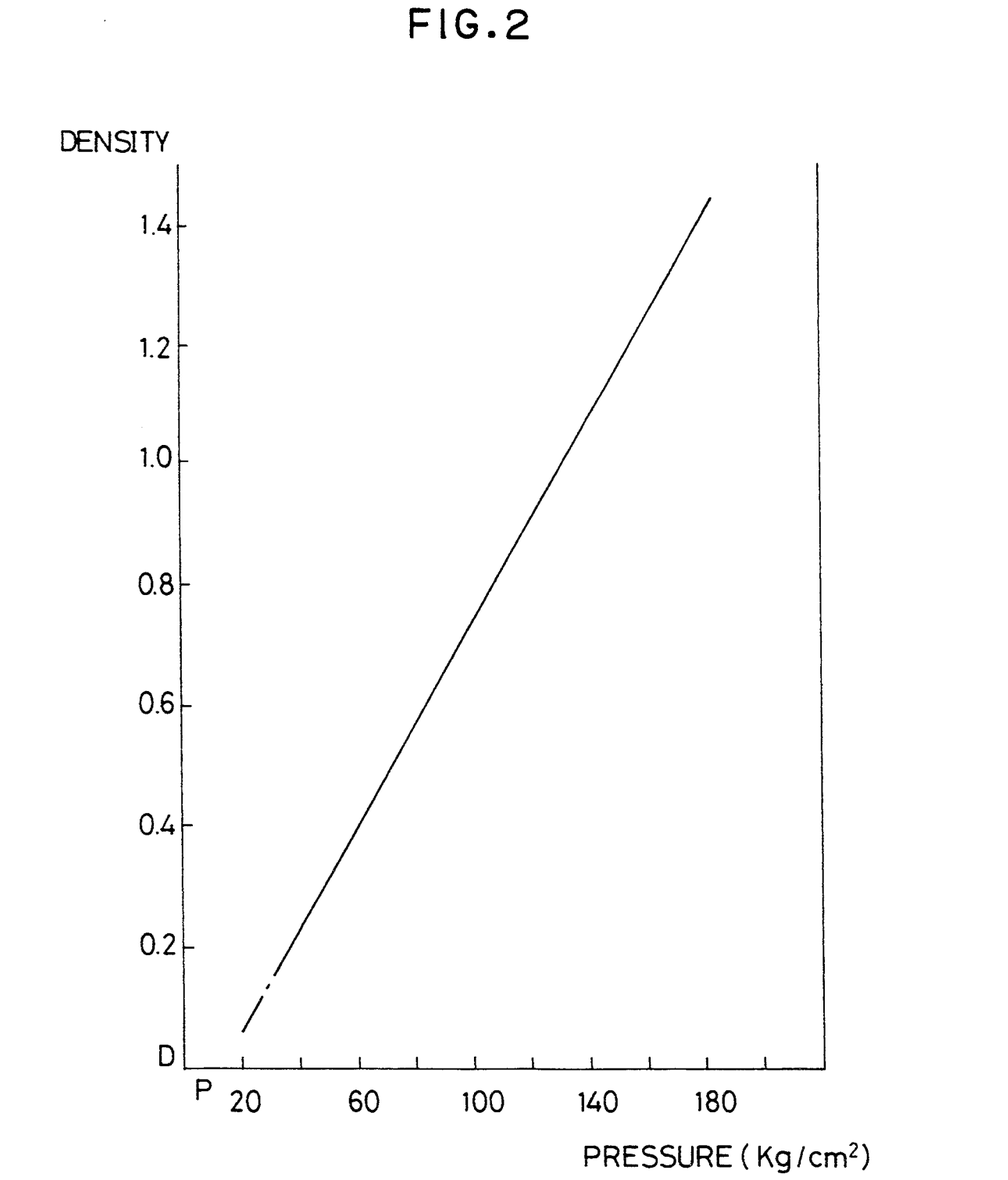
FIG. 2 is a graph showing an interrelation between the pressure P applied on the pressure-sentive recording sheet and the density of color developed in the sheet.

FIG. 1 is a sectional view showing a portion (marginal or peripheral portion) of one embodiment of the invention, and FIG. 2 shows the change in color density in terms of the applied pressure. In the Figures, reference numeral 10 designates a transparent synthetic resin support sheet which is, for example, made of a PET (polyethylene terephthalate) film having a thickness of 25 $\mu$m. Reference numeral 12 designates a color developer layer which is formed by coating a dispersion containing montmorillonnite sulfate (obtained by treating acid terra alba (montmorillonnite) with sulfuric acid) in an aqueous sodium hydroxide over one face (obverse side) of the support sheet 10, followed by drying.

Reference numeral 14 designates a color former layer overlaid on the color developer layer 12, and is formed by coating a color forming agent, such as 1-phenyl-1-xylylethane, in a microcapsulated condition in an oil. It is noted hereby that the microcapsules of the color former include microcapsules having varied strengths or resistances to be ruptured upon application of pressure. As some of the capsules are ruptured, depending on the pressure applied on the recording sheet, the color former contained in the ruptured capsules is absorbed together with the oil by the color developer to develop a color, red in the illustrated embodiment. The density of the thus developed color becomes thicker as the applied pressure is increased. FIG. 2 shows the change in density D of the developed color in terms of the applied pressure D.

More specifically, the pressure-sensitive recording sheet according to the invention makes use of coloring upon application of pressure, color development being resulted by the contact between the color former contained in the ruptured microcapsules and the color developer in the color developer layer 12. The microcapsules contained in the color former layer 12 are a mixture of a group of microcapsules respectively having different wall thicknesses to be ruptured upon application of different pressures. In other words, the number of capsules ruptured by the application of a particular pressure is intentionally differentiated. As the result of such construction, the density of color, which is developed by the reaction between the color former flowing out of the ruptured capsules and the color developer, developed by the application of a certain pressure is in some proportional interrelationship with the pressure applied on the pressure-sensitive recording sheet.

The coloring agent is a colorless compound which develops some color upon contact with a solid acid, examples being electron-donating organic compounds. On the other hand, the color developer is a solid acid, more specifically an electron-accepting solid acid. More detailed description of microcapsules, color formers or coloring agents and color developers which may be used in this invention will be found, for example, in Japanese Patent Publication No. 24852/1982 (corresponding to U.S. Pat. No. 4,002,060) and Japanese Patent Publication No. 16654/1984 (corresponding to U.S. Pat. No. 4,132,112). The descriptions in the specifications of these prior Patents will be incorporated herein by references.

Reference numeral 16 designates a first water-impermeable layer or backside waterproof layer which may be made of a transparent synthetic resin film such as PET film, similar to the film forming the support sheet 10, having a thickness of, for example, 16 $\mu$m. A tackifying adhesive is coated on one face, the face opposing to the support sheet 10, of the first water-impermeable layer 16 to form an adhesive layer 18. Thus, the first water-impermeable layer 16 is applied on one face (the face opposing to the face to which the color developer layer 12 is applied) of the support sheet 10 through this adhesive layer 18.

Reference numeral 20 designates a second water-impermeable layer or obverse waterproof layer which may be made of a transparent synthetic resin film such as PET film, similar to the film forming the first water-impermeable layer 16, having a thickness of, for example, 16 $\mu$m. This second water-impermeable layer 20 is overlaid on the color former layer 14 and has the peripheral margin sealingly adhering to the adhesive layer 18 of the first water-impermeable layer 16. It is desirous that entire marginal portions of both water-impermeable layers 16 and 20 are sealed under a sufficiently reduced pressure.

As should be appreciated by those skilled in the art, the pressure-sensitive recording sheet 22 of this embodiment is improved in waterproof property and exhibits high reliability in use, since the pressure-sensitive composite recording sheet structure 15 composed of the support sheet 10, the color developer layer 12 and the color former layer 14 is liquid-tightly sealed by means of the first water-impermeable layer 16 and the second water-impermeable layer 20. Moreover, since one of the water-impermeable layer, the first water-impermeable layer 16 in the illustrated embodiment, is closely adhering to the backside of the support sheet 10, the layer 16 is prevented from displacement relative to and delamination from the support sheet 10. With the construction as aforementioned, the second water-impermeable layer 20 is also prevented from relative displacement to the support sheet 10, since the marginal or peripheral portions thereof are fixedly adhering to the marginal or peripheral portions of the first water-impermeable layer 16.

Second Embodiment

Figure 3:
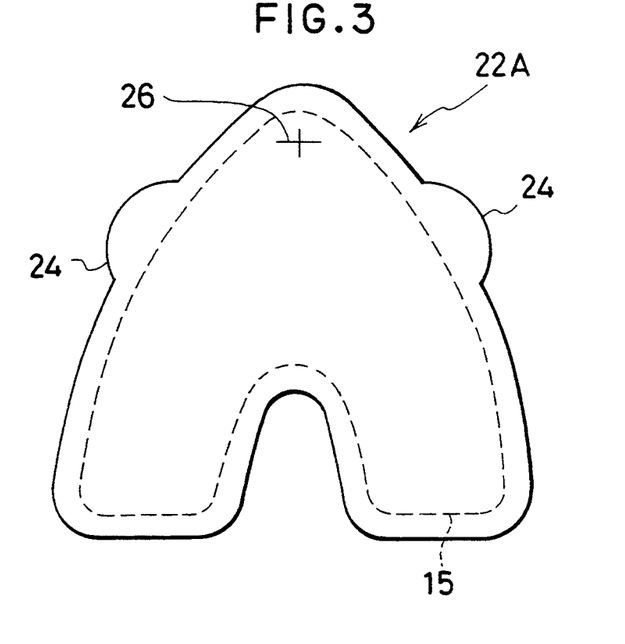
FIG. 3 is a plan view of an occlusion pressure detecting sheet according to the second embodiment of the invention.

FIG. 3 is a plan view of the occlusion pressure detecting sheet 22A according to the second embodiment of the invention, the layer structure and the process for producing the same are similar to those of the pressure-sensitive recording sheet 22 (see FIG. 1) according to the first embodiment. However, this second embodiment differs from the first embodiment in that the pressure-sensitive composite recording sheet structure 15 composed of the support sheet 10, the color developer layer 12 and the color former (contained in the microcapsulated condition) layer 14 is cut to have a generally horseshoe, lancet arch or cusp pattern as shown by the broken line in FIG. 3. More particularly, the sheet 22A has a pattern or shape to expand substantially co-extensive with the dental arch of a human being.

The pressure-sensitive composite recording sheet structure 15 may be prepared by cutting a generally horseshoe-like pattern from a web of composite sheet structure 15 which is composed of the support sheet 10, the color developer layer 12 and the color former (contained in the microcapsulated condition) layer 14. Alternatively, the support sheet 10 is initially cut to have a generally horseshoe-like pattern on which the color developer layer 12 and the color developer layer 14 are lamianted successively.

The finished occlusion pressure detecting sheet 22A is prepared by covering both faces of the composite sheet structure 15 by first and second water-impermeable layers 16 and 20 which are then liquid-tightly sealed along the entire periphery. Thus, the occlusion pressure detecting sheet 22A is completely sealed and protected by the first and second water-impermeable layers 16 and 20. Accordingly, the finished product has a perfect waterproof property to exclude the influence on coloring property thereof even if saliva or other liquids in the oral cavity might stick thereto, thereby improving in reliability.

Since one of the water-impermeable layer, the first water-impermeable layer 16 in the illustrated embodiment, is closely adhering to the backside of the support sheet 10, the layer 16 is prevented from displacement relative to and delamination from the support sheet 10. With the construction as aforementioned, the second water-impermeable layer 20 is also prevented from relative displacement to the support sheet 10, since the marginal or peripheral portions thereof are fixedly adhering to the marginal or peripheral portions of the first water-impermeable layer 16.

The occlusion pressure detecting sheet 22A shown in FIG. 3 has lugs 24, 24 integrally protruding from the outer periphery of the marginal portion at which the first and second water-impermeable layers 16 and 20 are directly adhering with each other, with the composite sheet structure 15 being contained internally of the marginal portion. These lugs 24, 24 are provided to facilitate the dentist to pick up the sheet 22A by his fingers to position the sheet 22A in situ by placing the cuspids of the patient thereon. A mark 26 is provided at the vicinity of the tip end of the composite sheet structure 15 so that the sheet 22A is positioned in situ by placing the incisor of the patient thereon.

Figure 4:
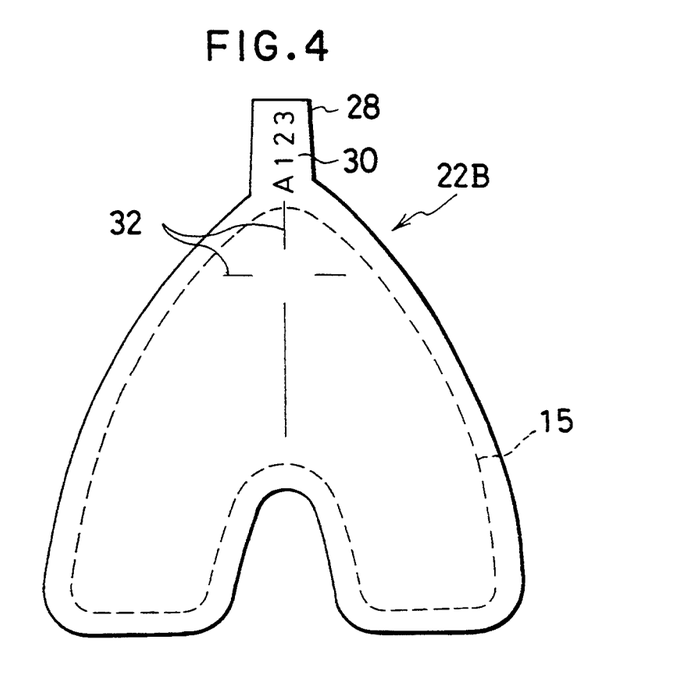
FIG. 4 is a plan view of a modified occlusion pressure detecting sheet according to the second embodiment of the invention.

An occlusion pressure detecting sheet 22B shown in FIG. 4 has a tag 28 integrally protruding from the portion vicinal to the tip end (at the portion on which the center of the dental arch of the patient is placed). A mark 30 for identifying the particular patient is attached to the tag 28. Also provided are marks 32, similar to the mark 26 of the embodiment shown in FIG. 3, so that the incisors of the patient are placed thereon to position the sheet 22B in situ.

Each of the occlusion pressure detecting sheets 22A, 22B is inserted into the opened mouth of the patient while holding the same by picking the lug 24 or the tag 28 and fitted with the maxilliary dental arch by placing the incisors of the patient on the mark 26 or 32 or placing the cuspids of the patient on the lugs 24. Then, as the patient bites the sheet 22A or 22B gently, the pressure developed between the upper and lower dental arches is applied on the pressure-sensitive composite recording sheet structure 15 so that the portions of the sheet 15 on which pressures are applied are colored with the densities in proportion to the applied pressures. In the illustrated embodiment, the developed color is red.

The dentist can know the distribution of the occlusion pressures directly by observing the density distribution of the thus developed color. Accordingly, by observing the sheet 22A or 22B, the condition of occlusion between the upper and lower dental arches can be precisely detected to facilitate the determination on the proper course of treatment.

The image on the sheet 22A or 22B may be read by a scanner. In detail, the color image developed by the application of occlusion pressure is read by the scanner and the image signals are processed through a computer to know the distribution of occlusion pressure or to effect other necessary analyses. However, due to irregular deformation on the surface of the sheet 22A or 22B, such deformation resulting by the contact with the teeth of the patient, the light reflected by the irregular surface of the sheet is diffused to make it difficult to read the colored image accurately at the step of reading the image by the scanner.

Figure 5:
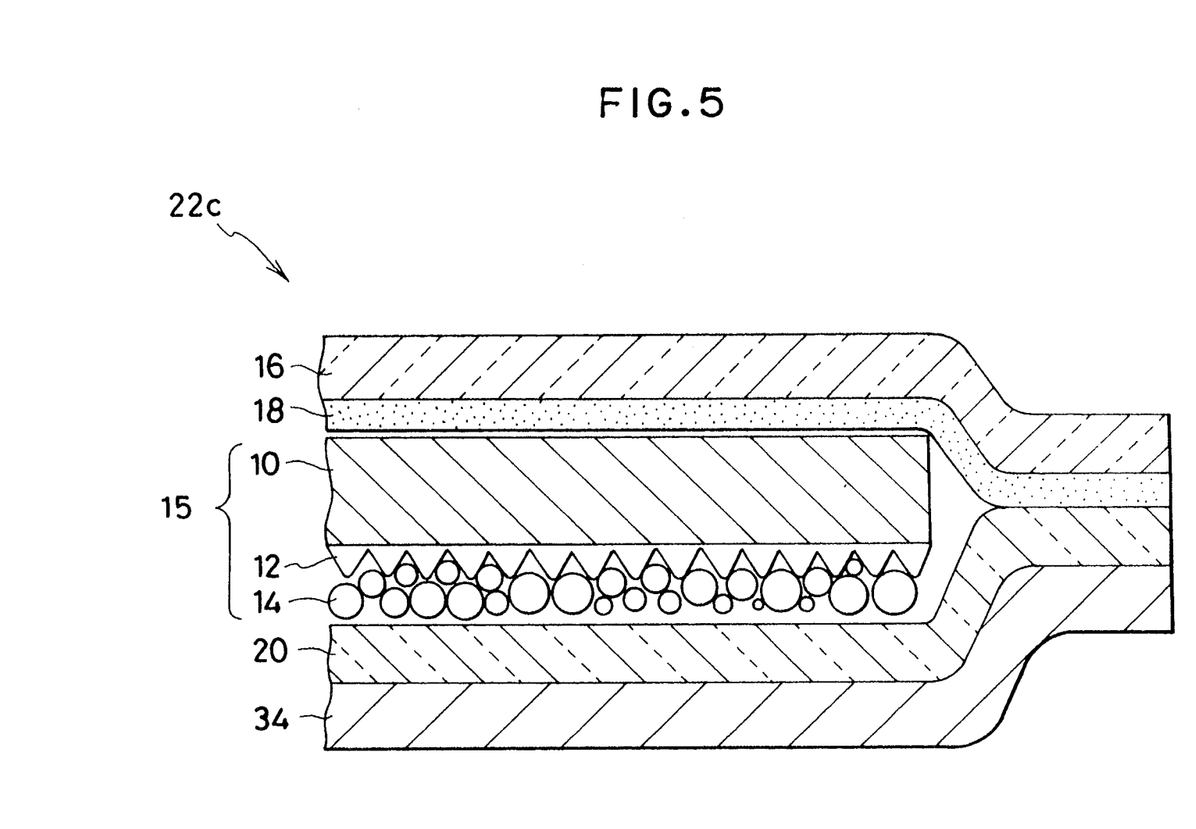
FIG. 5 is a sectional view showing a portion (marginal or peripheral portion) of the occlusion pressure detecting sheet according to a further modification of the second embodiment of the invention.

A modified occlusion pressure detecting sheet 22C, which is conceived to be more conveniently used when the sheet is read by a scanner, is shown in FIG. 5. The sheet 22C has a structure similar to that of the sheet 22 shown in FIG. 1, except that a thin wax coating layer 34 is overcoated on the second synthetic resin water-impermeable layer 20. The wax coating layer 34 may be formed by coating a dental paraffin wax (JIS-T-6502) to have a thickness of, for example, 50 to 75 μm.

When the sheet 22C having the wax coating layer 34 is applied for practical use, the portions of the overlying wax coating layer 34 which contact the teeth of the patient are expelled outwards or shoved aside. As a result, the wax coating in the layer 34 is expelled only at the portions where the tooth tips are engaged to develop color in the pressure-sensitive composite recording sheet structure 15, while the wax coating is left at those portions where no occlusion pressure is applied.

At the step of reading the colored image on the sheet 22C by the scanner, the image formed by the colored portions, from which wax coating layer 34 is expelled, is read. Although irregular undulation has been formed by the teeth on the surface of the sheet 22C, the wax coating layer 34 serves to attenuate the influence by the diffused reflection (which is caused by the presence of such undulation or convex and concave portions), whereby the precise colored image is read out.

The kind, thickness and color of the wax used to form the wax coating layer 34 is not limited only to those of the wax used in the illustrated embodiment, and the appropriate thickness of the wax coating is varied depending on the used wax and may be determined empirically in consideration of the performance characteristics of the used scanner. Although it suffices that the wax coating layer 34 is provided only at one side from which the color density is read, the sheet structure provided with wax coating layers on both sides or faces thereof is included within the scope of the invention.

As has been described hereinabove, the second embodiment of the invention comprises a generally horseshoe-shaped pressure-sensitive composite recording sheet structure 15 enveloped within waterproof layers 16, 20 which are sealed liquid-tightly. Accordingly, by the use of the second embodiment described above, the positions and extents of the occluding pressures applied by the teeth of the patient can be readily detected by referring to the positions and densities of the color developed on the pressure-sensitive composite sheet 15 to obtain the data which are effectively utilizable for the precise diagnosis on the occlusion condition and for the determination of subsequent course of treatment of the teeth.

The patient can be diagnosed with ease by biting the occlusion pressure detecting sheet only one time on the one hand, and on the other hand the dentist can readily judge the interrelation between the occuluded positions and the occlusion pressures only by observing the occlusion pressure detecting sheet without the need of watching the oral cavity of the patient during the test.

It is preferred to provide a mark for positioning the sheet relative to the incisor of the patient. It is also preferred to provide lugs, which are to be placed under the cuspids, beyond the outer periphery for convenient inserting and positioning of the sheet while placing the lugs under the cuspids of the patient. A more convenient sheet is prepared, within the scope of the invention, by the provision of a tag to be pinched for inserting and pulling out the sheet and a mark for the identification of the patient.

By the provision of a wax coating layer on the exposed surface of the synthetic resin water-impermeable layer or obverse waterproof layer, the colored image can be more precisely read by a scanner since the wax coating layer prevents the reduction in accuracy at the step of reading the colored image due to diffussed reflection of light by the presence of undulation formed by the occluding teeth.

Third Embodiment

Figure 6:
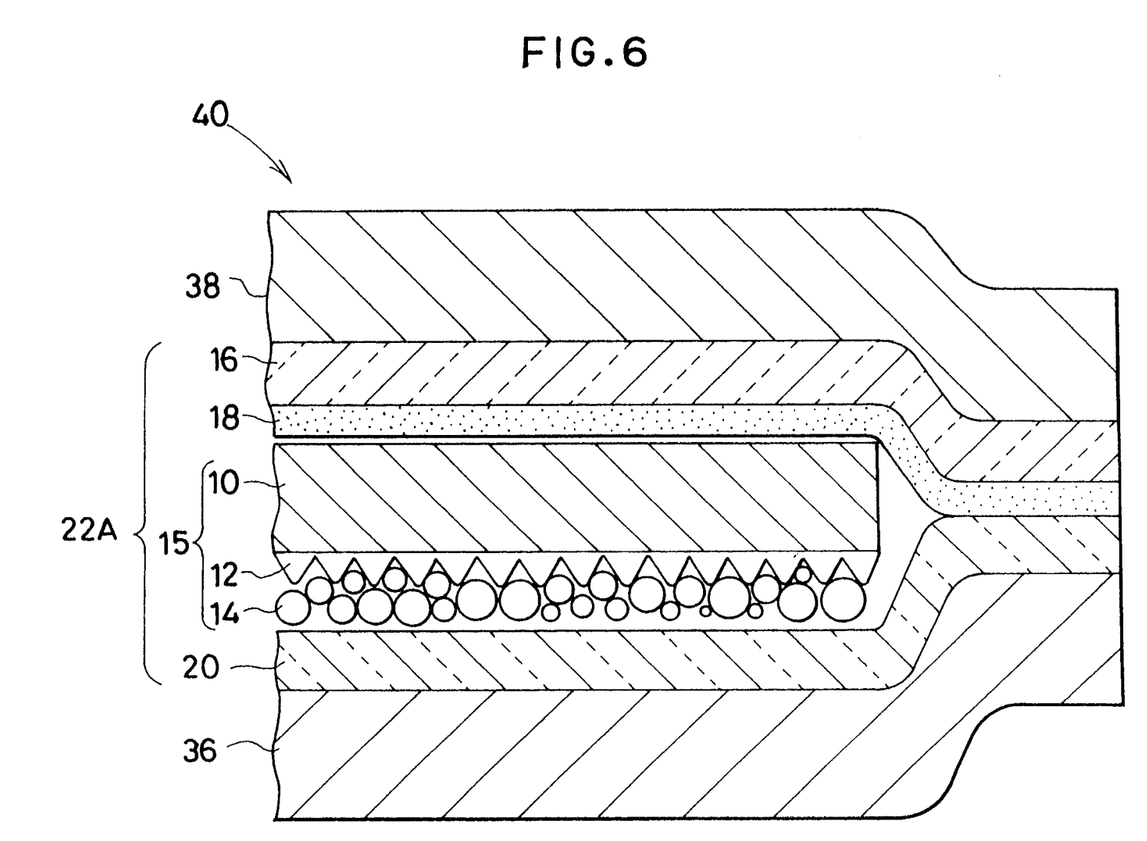
FIG. 6 is a sectional view showing a portion (marginal or peripheral portion) of the occlusion pressure detecting sheet according to the third embodiment of the invention.

FIG. 6 is a sectional view showing the peripheral portion of an occlusion pressure detecting sheet 40 according to a third embodiment of the invention. In detail, the occlusion pressure detecting sheet 40 of the third embodiment has wax coating layers 36, 38 applied over both surfaces of the occlusion pressure detecting sheet 22A or 22B (see FIGS. 1, 3 and 4) of the second embodiment.

The structure other than the wax coating layers 36, 38 is similar to that of the second embodiment, so that a pressure-sensitive composite recording sheet structure 15 composed of the support 10, the color developer layer 12 and the color former (contained in the microcapsulated condition) layer 14 is shaped to have a generally horseshoe-like pattern so as to cover the area of the dental arch of a human being, as shown by the broken line in FIG. 3.

This generally horseshoe pattern sheet 22A is protected from being wetted by water by the waterproof or water-impermeable layers 16, 20 on which the wax coating layers 36, 38 are coated. Each of the wax coating layers 36, 38 is formed by uniformly coating a dental paraffin wax (JIS-T-6502) to have a thickness of, for example, 0.35±0.3 mm. It is desirous that each of the wax coating layers 36, 38 has a color substantially complementary to the color developed in the pressure-sensitive composite recording sheet structure 15. In the illustrated example wherein the coloring by the color former is red, a blue to green wax is preferably used. The finished occlusion pressure detecting sheet 40 is prepared by coating the wax coating layers 36 and 38.

The occlusion pressure detecting sheet 40 is inserted into the opened mouth of a patient while holding the same by pinching the lugs 24 or the tag 28 and fitted within the mouth by positioning the same by placing the mark 26 or the mark 32 below the incisor of the maxilliary dental arch or by placing the lugs below the cuspids of the maxilliary arch so that it is engaged evenly with the maxilla. As the patient bites the sheet 40, occlusion pressures between the upper and lower teeth are applied on the wax coating layers 36, 38 so that the pattern of the entire dental arch is recorded as the concaved and convexed traces on these wax coating layers 36, 38. At the same time, the occlusion pressures between the upper and lower teeth are applied on the pressure-sensitive composite recording sheet structure 15 so that the portions on which the pressures are applied are colored, in red in the illustrated example, to have densities varied depending on the applied pressures.

The dentist can know the condition of the tooth row of the patient by inspecting the traces of the dental arches recorded on the wax coating layers 36, 38 of the occlusion pressure detecting sheet 40, and also know the extent of occlusion pressures from the color densities developed on the pressure-sensitive composite sheet structure 15. Thus, the dentist can have precise knowledge about the occlusion condition of the patient and can determine the proper course of treatment in view of the thus obtained knowledge.

Figure 7:
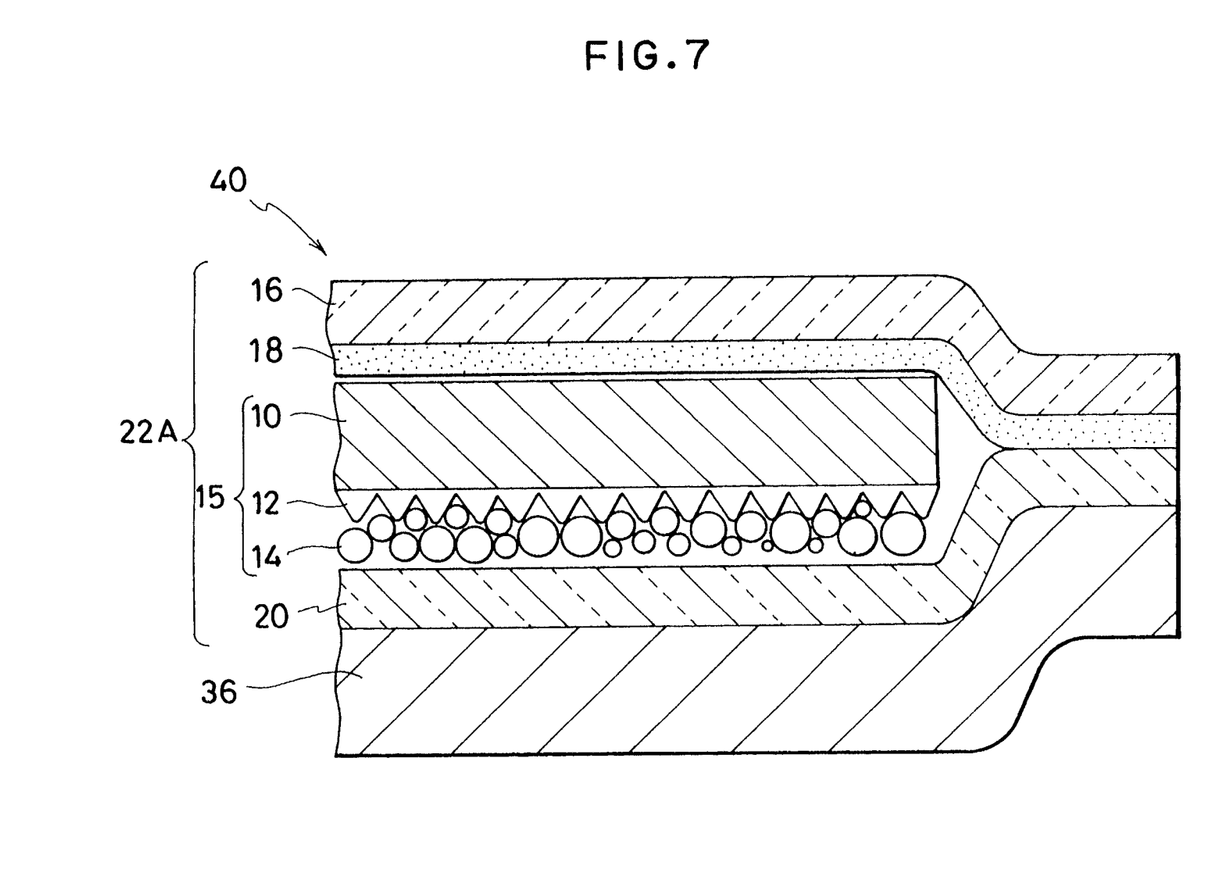
FIG. 7 is a sectional view showing a portion (marginal or peripheral portion) of the occlusion pressure detecting sheet according to another modification of the third embodiment of the invention.

FIG. 7 is a sectional view showing a further embodiment of the invention. This embodiment is similar to the embodiment shown in FIG. 6, except that one wax coating layer 38 is omitted while the other wax coating layer 36 is left. When a wax coating layer is provided on only one of the surfaces of the sheet 22A, the wax coating layer 36 may be overlaid on the surface of the color former layer 14, whereby the traces of the teeth forming the concaved and convexed dental arch pattern and the color image in the pressure-sensitive composite recording sheet structure 15 can be visually confirmed in the overlapped condition to make it easy to confirm the relative positioning.

Alternatively, only one wax coating layer 38 may be provided at the side or face close to the support sheet 10. This alternative construction is conveniently used when the concaved and convexed dental arch pattern and the colored image of the pressure-sensitive composite sheet structure 15 are read at separate steps, since the wax coating layer 38 does not serve as an obstacle to the operation of sensing the colored image. In such an embodiment, it is preferred that the support sheet 10 is opaque.

The occlusion pressure detecting sheet is preferably provided with a mark for discriminating the right side from the left side and/or a mark for discriminating the reverse side from the obverse side. For example, the right half of the sheet may have a shape differentiated from the shape of the left half (i.e. the sheet has an unsymmetrical shape), or a punched hole may be provided in either one of the right or left half, or the areas of the right and left lugs shown in FIG. 3 may be differentiated from each other.

As has been described hereinabove, the third embodiment has a wax coating layer on at least one of the outer waterproof or water-impermeable layers 16, 18 containing therein a generally horseshoe shape pressure-sensitive composite sheet structure 15, whereby the pattern of the dental arch can be known by inspecting the concaved and convexed traces of teeth recorded on the wax coating layer and the pressures between the occluding upper and lower teeth can be known by inspecting the color densities so as to obtain effective data usable for the precise diagnosis on the occlusion condition of the teeth and for the establishment of a proper course of treatment.

The patient can be diagnosed with ease by biting the occlusion pressure detecting sheet only one time on the one hand, and on the other hand the dentist can readily judge the interrelation between the occluded positions and the occlusion pressures only by observing the occlusion pressure detecting sheet without the need of watching the oral cavity of the patient during the test.

It is preferred that the color developed by the pressure-sensitive composite sheet structure is differentiated from the color of the wax coating layer, and particularly the color of the former be complementary to the color of the latter so as to enable easier confirmation or distinguishing operation. It is desirous that the occlusion pressure detecting sheet if provided with a mark for placing thereon the incisor of the patient.

It is also preferred to provide lugs, which are to be placed under the cuspids, beyond the outer periphery for convenient inserting and positioning of the sheet while placing the lugs under the cuspids of the patient. A more convenient sheet is prepared, within the scope of the invention, by the provision of a tag which is pinched for inserting and pulling out the sheet, a mark for the identification of the patient, a mark for discriminating the right side from the left side, and a mark for discriminating the reverse side from the obverse side.

What is claimed is:

1. An occlusion pressure detecting sheet, comprising:
    (a) a synthetic resin support sheet having a horseshoe shape adapted to extend along the dental arch;
    (b) a color developer layer co-extensively coated on one face of said support sheet;
    (c) a color former layer overcoated on said color developer layer and containing a microcapsulated color former;
    (d) a first water-impermeable layer adhering on the other face of said support sheet through an adhesive; and
    (e) a transparent second water-impermeable layer covering directly over said color former layer; and
   wherein the outer peripheries of said first and second water-impermeable layers are liquid-tightly closed to protect said support sheet, said color developer layer and said color former layer from attack by any aqueous liquid.

2. The occlusion pressure detecting sheet according to claim 1, wherein a positioning mark is provided for positioning said occlusion pressure detecting sheet in situ relative to the dental arch of the patient.

3. The occlusion pressure detecting sheet according to claim 1, further comprising lugs integrally protruding beyond the outer periphery of said occlusion pressure detecting sheet for positioning said occlusion pressure detecting sheet in situ relative to the cuspids in the dental arch of the patient.

4. The occlusion pressure detecting sheet according to claim 1, further comprising a tag integrally protruding from the substantial center of said occlusion pressure detecting sheet.

5. The occlusion pressure detecting sheet according to claim 1, further comprising a mark for identifying the patient.

6. The occlusion pressure detecting sheet according to claim 1, further comprising a wax coating layer overlaid on the exposed surface of said second water-permeable layer.

7. The occlusion pressure detecting sheet according to claim 6, wherein said wax coating layer has a thickness of from 50 to 75 $\mu$m.

8. An occlusion pressure detecting sheet, comprising:
    (a) a synthetic resin support sheet having a horseshoe shape adapted to extend along a dental arch;
    (b) a color developer layer co-extensively coated on one face of said support sheet;
    (c) a color former layer overcoated on said color developer layer and containing a microcapsulated color former;
    (d) a first water-impermeable layer adhering on the other face of said support sheet through an adhesive;
    (e) a transparent second water-impermeable layer covering directly over said color former layer; and
    (f) a wax coating layer laminated over at least one of said first and second water-permeable layers;
   whereby an occlusion pressure of a patient is detected by determining the density of color developed by the reaction between said color former and said color developer layer under the occlusion pressure of the patient, and the pattern of the dental arch of the patient is detected by observing the trace of the patient's teeth left on said wax coating layer.

9. The occlusion pressure detecting sheet according to claim 8, wherein said wax coating layer has a thickness in the range of $0.35 \pm 0.03$ mm.

10. The occlusion pressure detecting sheet according to claim 8, wherein said wax coating layer has a color which is complementary to the color developed by the reaction between said color former and said color developer layer.

11. The occlusion pressure detecting sheet according to claim 8, wherein a positioning mark is provided for positioning said occlusion pressure detecting sheet in situ relative to the dental arch of the patient.

12. The occlusion pressure detecting sheet according to claim 8, further comprising lugs integrally protruding beyond the outer periphery of said occlusion pressure detecting sheet for positioning said occlusion pressure detecting sheet in situ relative to the cuspids in the dental arch of the patient.

* * * * *

UNITED STATES PATENT AND TRADEMARK OFFICE
CERTIFICATE OF CORRECTION

PATENT NO.   : 5,395,239
DATED        : March 7, 1995
INVENTOR(S)  : Tomoaki KOMATSU et al It is certified that error(s) appears in the above-identified patent and that said Letters Patent is hereby corrected as shown below:

Title page, left column, after line [22], insert:

--[30]    Foreign Application Priority Data

Oct. 15, 1995 [JP]    Japan ............... 4-302974
    Oct. 15, 1992 [JP]    Japan ............... 4-302975
    Oct. 15, 1992 [JP]    Japan ............... 4-302976--.

Signed and Sealed this

Thirtieth Day of May, 1995

Attest:

BRUCE LEHMAN

*Attesting Officer*    *Commissioner of Patents and Trademarks*